(12) United States Patent
Boutoussov et al.

(10) Patent No.: US 11,103,309 B2
(45) Date of Patent: Aug. 31, 2021

(54) MULTIPLE BEAM LASER TREATMENT DEVICE

(71) Applicant: Biolase, Inc., Irvine, CA (US)

(72) Inventors: Dmitri Boutoussov, Dana Point, CA (US); Vladimir Netchitailo, Livermore, CA (US); Amado Carino, Laguna Beach, CA (US)

(73) Assignee: BIOLASE, INC., Irvine, CA (US)

( * ) Notice: Subject to any disclaimer, the term of this patent is extended or adjusted under 35 U.S.C. 154(b) by 303 days.

(21) Appl. No.: 16/197,172

(22) Filed: Nov. 20, 2018

(65) Prior Publication Data

US 2019/0159838 A1 May 30, 2019

Related U.S. Application Data

(63) Continuation of application No. 14/610,650, filed on Jan. 30, 2015, now Pat. No. 10,130,424.

(Continued)

(51) Int. Cl.
*A61B 18/20* (2006.01)
*A61N 5/06* (2006.01)
(Continued)

(52) U.S. Cl.
CPC ........... *A61B 18/20* (2013.01); *A61N 5/0624* (2013.01); *A61B 2018/00577* (2013.01);
(Continued)

(58) Field of Classification Search
CPC .......... A61B 18/20; A61B 2018/00577; A61B 2018/00601; A61B 2018/2065; A61B 2018/208; A61N 5/0624; A61N 2005/067
(Continued)

(56) References Cited

U.S. PATENT DOCUMENTS 5,139,494 A  8/1992  Freiberg
5,304,167 A  4/1994  Freiberg
(Continued)

FOREIGN PATENT DOCUMENTS

CA  2945691  5/2015
CN  101442951  5/2009
(Continued)

OTHER PUBLICATIONS

Korean Intellectual Property Office; PCT International Search Report, Issued in Connection to PCT/US2015/013925; dated Apr. 27, 2015; 8 pages; Korea.

(Continued)

*Primary Examiner* — Aaron F Roane
(74) *Attorney, Agent, or Firm* — Greenberg Traurig, LLP

(57) ABSTRACT

Embodiments of the invention include a treatment device and corresponding treatment method for laser wound healing, the device and method making use of the simultaneous action of multiple laser types and laser wavelengths which are applied at human tissue. The treatment device generally includes a laser system and a hand-piece which is coupled to the laser system. The hand-piece is designed so that one or multiple laser beams are applied at relatively small spot and at a relatively high power level, and are surrounded by a relatively large spot of another laser beam with a relatively low power level. In a preferred implementation, the hand-piece is adapted to facilitate the emission of first and second laser beams together with a third laser beam which is delivered at a different spatial profile in comparison to the first and second laser beams.

20 Claims, 2 Drawing Sheets

Related U.S. Application Data

(60) Provisional application No. 61/934,599, filed on Jan. 31, 2014.

(51) Int. Cl.
*A61B 18/00* (2006.01)
*A61N 5/067* (2006.01)

(52) U.S. Cl.
CPC .............. *A61B 2018/00601* (2013.01); *A61B 2018/208* (2013.01); *A61B 2018/2065* (2013.01); *A61N 2005/067* (2013.01)

(58) Field of Classification Search
USPC .......................................................... 606/13
See application file for complete search history.

(56) References Cited

U.S. PATENT DOCUMENTS

| | | | |
|---|---|---|---|
| 5,510,895 A | 4/1996 | Sahagen | |
| 5,526,112 A | 6/1996 | Sahagen | |
| 5,540,676 A | 7/1996 | Freiberg | |
| 5,581,648 A | 12/1996 | Sahagen | |
| 5,741,247 A | 4/1998 | Rizoiu et al. | |
| 5,785,521 A | 7/1998 | Rizoiu et al. | |
| 6,231,567 B1 | 5/2001 | Rizoiu et al. | |
| 6,254,597 B1 | 7/2001 | Rizoiu et al. | |
| 6,288,499 B1 | 9/2001 | Rizoiu et al. | |
| 6,350,123 B1 | 2/2002 | Rizoiu et al. | |
| 6,389,193 B1 | 5/2002 | Kimmel et al. | |
| 6,561,803 B1 | 5/2003 | Rizoiu et al. | |
| 6,567,582 B1 | 5/2003 | Rizoiu et al. | |
| 6,610,053 B1 | 8/2003 | Rizoiu et al. | |
| 6,669,685 B1 | 12/2003 | Rizoiu et al. | |
| 6,744,790 B1 | 6/2004 | Tilleman et al. | |
| 6,821,272 B2 | 11/2004 | Rizoiu et al. | |
| 7,108,693 B2 | 9/2006 | Rizoiu et al. | |
| 7,184,184 B2 | 2/2007 | Debenedictis et al. | |
| 7,187,822 B2 | 3/2007 | Rizoiu et al. | |
| 7,196,831 B2 | 3/2007 | Broome et al. | |
| 7,265,884 B2 | 9/2007 | Debenedictis et al. | |
| 7,282,060 B2 | 10/2007 | Debenedictis et al. | |
| 7,288,086 B1 | 10/2007 | Andriasyan | |
| 7,295,358 B2 | 11/2007 | Debenedictis et al. | |
| 7,320,594 B1 | 1/2008 | Rizoiu et al. | |
| 7,372,606 B2 | 5/2008 | Broome et al. | |
| 7,411,711 B2 | 8/2008 | Debenedictis et al. | |
| 7,415,050 B2 | 8/2008 | Rizoiu et al. | |
| 7,421,186 B2 | 9/2008 | Boutoussov et al. | |
| 7,424,199 B2 | 9/2008 | Rizoiu et al. | |
| 7,480,086 B2 | 1/2009 | Debenedictis et al. | |
| 7,486,426 B2 | 2/2009 | Broome et al. | |
| 7,557,975 B2 | 7/2009 | Debenedictis et al. | |
| 7,563,226 B2 | 7/2009 | Boutoussov | |
| 7,578,622 B2 | 8/2009 | Boutoussov | |
| 7,620,290 B2 | 11/2009 | Rizoiu et al. | |
| 7,630,420 B2 | 12/2009 | Boutoussov | |
| 7,636,186 B2 | 12/2009 | Debenedictis et al. | |
| 7,646,522 B2 | 1/2010 | Broome et al. | |
| 7,652,810 B2 | 1/2010 | Debenedictis et al. | |
| 7,702,196 B2 | 4/2010 | Boutoussov et al. | |
| 7,924,488 B2 | 4/2011 | Broome et al. | |
| 7,957,440 B2 | 6/2011 | Boutoussov | |
| 7,982,936 B2 | 7/2011 | Broome et al. | |
| 8,033,825 B2 | 10/2011 | Rizoiu et al. | |
| 8,152,797 B2 | 4/2012 | Boutoussov et al. | |
| 8,221,117 B2 | 7/2012 | Rizoiu et al. | |
| 8,419,719 B2 | 4/2013 | Rizoiu et al. | |
| 8,764,739 B2 | 7/2014 | Boutoussov et al. | |
| 2002/0014855 A1 | 2/2002 | Rizoiu et al. | |
| 2002/0149324 A1 | 10/2002 | Rizoiu et al. | |
| 2003/0216719 A1 | 11/2003 | Debenedictis et al. | |
| 2003/0228094 A1 | 12/2003 | Rizoiu et al. | |
| 2004/0068256 A1 | 4/2004 | Rizoiu et al. | |
| 2004/0082940 A1 | 4/2004 | Black et al. | |
| 2004/0092925 A1 | 5/2004 | Rizoiu et al. | |
| 2005/0049582 A1 | 3/2005 | Debenedictis et al. | |
| 2005/0076118 A1 | 4/2005 | Burghardt et al. | |
| 2005/0141068 A1 | 6/2005 | Debenedictis et al. | |
| 2005/0154380 A1 | 7/2005 | Debenedictis et al. | |
| 2005/0256516 A1 | 11/2005 | Boutoussov | |
| 2005/0256517 A1 | 11/2005 | Boutoussov | |
| 2005/0259306 A1 | 11/2005 | Broome et al. | |
| 2005/0281530 A1 | 12/2005 | Rizoiu et al. | |
| 2005/0285928 A1 | 12/2005 | Broome et al. | |
| 2006/0043903 A1 | 3/2006 | Rizoiu et al. | |
| 2006/0119920 A1 | 6/2006 | Debenedictis et al. | |
| 2006/0126680 A1 | 6/2006 | Boutoussov | |
| 2006/0132882 A1 | 6/2006 | Debenedictis et al. | |
| 2006/0142745 A1 | 6/2006 | Boutoussov | |
| 2006/0217695 A1 | 9/2006 | Debenedictis et al. | |
| 2006/0217788 A1 | 9/2006 | Herron et al. | |
| 2006/0240381 A1 | 10/2006 | Rizoiu et al. | |
| 2006/0275016 A1 | 12/2006 | Boutoussov et al. | |
| 2007/0014322 A1 | 1/2007 | Rizoiu et al. | |
| 2007/0042315 A1 | 2/2007 | Boutoussov et al. | |
| 2007/0051293 A1 | 3/2007 | Austin | |
| 2007/0060917 A1 | 3/2007 | Andriasyan | |
| 2007/0104419 A1 | 5/2007 | Rizoiu et al. | |
| 2007/0145146 A1 | 6/2007 | Debenedictis et al. | |
| 2007/0158424 A1 | 7/2007 | Broome et al. | |
| 2007/0179481 A1 | 8/2007 | Frangineas et al. | |
| 2007/0190482 A1 | 8/2007 | Rizoiu | |
| 2007/0208328 A1 | 9/2007 | Boutoussov et al. | |
| 2007/0232264 A1 | 10/2007 | Burghardt et al. | |
| 2007/0263975 A1 | 11/2007 | Boutoussov et al. | |
| 2007/0265606 A1 | 11/2007 | Debenedictis et al. | |
| 2008/0014903 A1 | 1/2008 | Burghardt et al. | |
| 2008/0025672 A1 | 1/2008 | Boutoussov et al. | |
| 2008/0043306 A1 | 2/2008 | Debenedictis et al. | |
| 2008/0065057 A1 | 3/2008 | Andriasyan | |
| 2008/0068694 A1 | 3/2008 | Debenedictis et al. | |
| 2008/0069172 A1 | 3/2008 | Rizoiu et al. | |
| 2008/0088901 A1 | 4/2008 | Debenedictis et al. | |
| 2008/0112027 A1 | 5/2008 | Debenedictis et al. | |
| 2008/0138764 A1 | 6/2008 | Rizoiu | |
| 2008/0151953 A1 | 6/2008 | Rizoiu et al. | |
| 2008/0157690 A1 | 7/2008 | Rizoiu et al. | |
| 2008/0181261 A1 | 7/2008 | Boutoussov et al. | |
| 2008/0203280 A1 | 8/2008 | Rizoiu et al. | |
| 2008/0208178 A1 | 8/2008 | Debenedictis et al. | |
| 2008/0212624 A1 | 9/2008 | Boutoussov | |
| 2008/0219629 A1 | 9/2008 | Rizoiu et al. | |
| 2008/0252956 A1 | 10/2008 | Broome et al. | |
| 2008/0276192 A1 | 11/2008 | Jones et al. | |
| 2008/0317429 A1 | 12/2008 | Boutoussov et al. | |
| 2009/0043364 A1 | 2/2009 | Rizoiu et al. | |
| 2009/0075229 A1 | 3/2009 | Rizoiu et al. | |
| 2009/0104580 A1 | 4/2009 | Rizoiu et al. | |
| 2009/0118720 A1 | 5/2009 | Black et al. | |
| 2009/0141752 A1 | 6/2009 | Rizoiu et al. | |
| 2009/0225060 A1 | 9/2009 | Rizoiu et al. | |
| 2009/0275935 A1 | 11/2009 | McKee | |
| 2009/0281531 A1 | 11/2009 | Rizoiu et al. | |
| 2009/0298004 A1 | 12/2009 | Rizoiu | |
| 2010/0067081 A1 | 3/2010 | Broome et al. | |
| 2010/0086892 A1 | 4/2010 | Rizoiu et al. | |
| 2010/0100086 A1 | 4/2010 | Boutoussov et al. | |
| 2010/0125291 A1 | 5/2010 | Rizoiu et al. | |
| 2010/0145323 A1 | 6/2010 | Boutoussov et al. | |
| 2010/0151406 A1 | 6/2010 | Boutoussov et al. | |
| 2010/0185188 A1 | 7/2010 | Boutoussov et al. | |
| 2010/0233645 A1 | 9/2010 | Rizoiu | |
| 2011/0032958 A1 | 2/2011 | Rizoiu et al. | |
| 2011/0059417 A9 | 3/2011 | Rizoiu et al. | |
| 2011/0082526 A1 | 4/2011 | Rizoiu et al. | |
| 2011/0129789 A1 | 6/2011 | Rizoiu et al. | |
| 2011/0137302 A1 | 6/2011 | Broome et al. | |

(56) References Cited

U.S. PATENT DOCUMENTS

2012/0083772 A1  4/2012  Rubinfeld et al.
2013/0123648 A1  5/2013  Stampoulidis et al.

FOREIGN PATENT DOCUMENTS

| CN | 201832290 | 5/2011 |
| CN | 102106756 | 6/2011 |
| CN | 202522769 | 11/2012 |
| CN | 105980010 | 9/2016 |
| EP | 3099378 | 7/2016 |
| KR | 10-2016-0114658 | 10/2016 |
| WO | 2015117009 | 8/2015 |

OTHER PUBLICATIONS

Korean Intellectual Property Office; PCT Written Opinion of the International Searching Authority, Issued in Connection to PCT/US2015/013925; dated Apr. 27, 2015; 8 pages; Korea.
The State Intellectual Property Office of the Peoples Republic of China; Notification of the First Office Action, issued in connection to CN2015800067112; dated Mar. 2, 2018; 13 pages; China.
European Patent Office; Extended European Search Report, issued in connection to EP15742552.1; 8 pages; dated Jun. 28, 2017; Europe.

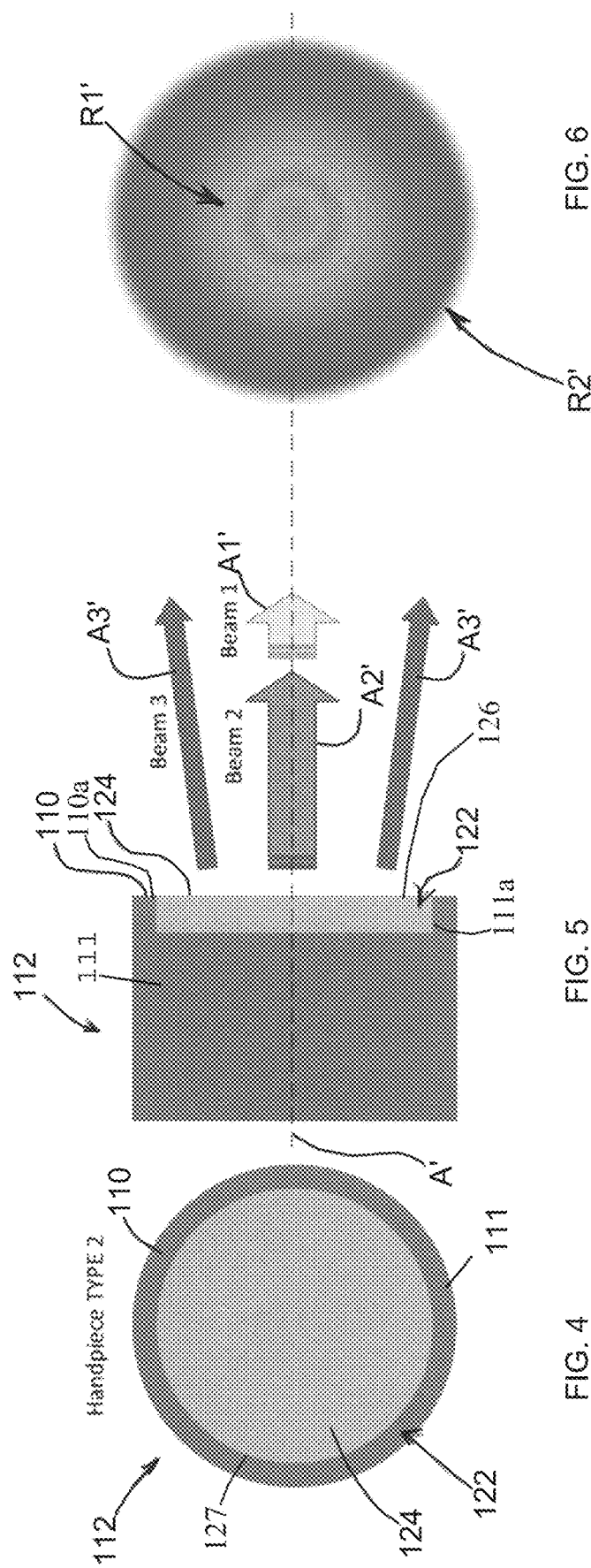

MULTIPLE BEAM LASER TREATMENT DEVICE

CROSS-REFERENCE TO RELATED APPLICATIONS

This application is a continuation application of U.S. application Ser. No. 14/610,650, entitled "MULTIPLE BEAM LASER TREATMENT DEVICE", filed Jan. 30, 2015, which claims the benefit of and priority to U.S. Provisional Application No. 61/934,599, entitled "MULTIPLE BEAM LASER TREATMENT DEVICE" filed Jan. 31, 2014, the entire contents of which are incorporated herein by reference.

BACKGROUND OF THE INVENTION

Field of the Invention

Embodiments of the invention relate generally to medical laser systems and, more particularly, to devices and methods for multiple beam laser treatment in which tissue sites are simultaneously exposed to different laser types and laser wavelengths for improved therapeutic effect.

2. Description of Art

Lasers find application in a variety of medical and dental treatment procedures, with some of the most common operations involving the cutting, ablation, disinfection or other treatment of tissue. Depending on the particular wavelength, output power, pulse width of the laser emission, and the absorptivity of the target tissue, varying biological materials from soft tissue such as muscles and skin, to hard tissue such as teeth and bones, can be cut and ablated. Laser systems with output power levels up to the tens of watts can be used for these applications, although lower powered laser systems with output power levels in the 10 milliwatt range can be used in microbicidal applications, tissue biostimulation applications, low-level light therapy, and other non-tissue-destructive applications.

A conventional laser system generally includes three primary components: a laser medium that generates the laser light, a power supply that delivers energy to the laser medium in the form needed to excite the same to emit coherent light, and an optical cavity or resonator that concentrates the light to stimulate the emission of laser radiation. Laser emissions can range from ultraviolet wavelengths, visible light wavelengths, to infrared wavelengths, depending on the type of laser medium utilized, whether the medium comprises one or more gases, chemicals, dyes, metal vapors, and whether the laser is solid state, or semiconductor, etc.

In high output power surgical laser applications, solid state type lasers are often used in which the laser medium is comprised of a solid host crystalline or glass structure that includes at least one dopant material. Particular dopant materials and the corresponding emission wavelengths are well known in the art. For example, in hard and soft tissue ablation applications, neodymium-doped yttrium aluminum garnet (Nd:YAG) lasers with an emission wavelength of about 1.064 µm, erbium-doped yttrium aluminum garnet (Er:YAG) lasers with an emission wavelength of 2.94 µm, and holmium-doped yttrium aluminum garnet (Ho:YAG) lasers are frequently utilized. Furthermore, erbium chromium doped yttrium, scandium, gallium garnet (Er, Cr:YSGG) lasers have been utilized successfully in medical treatment applications. Other laser media utilizing gasses such as carbon dioxide, argon, copper vapor lasers, and excimer media (e.g., using noble gas halides) have also been used with success.

During operation of a typical laser system, the laser medium (e.g., the doped solid host structure) is excited to a population inversion state with an optical pump such as a flash lamp that generates short-duration, intense, incoherent, full spectrum light. In the population inversion state, atoms of an elevated energy state exceed those of a lower energy state.

Instead of flash lamps, electrically powered diode lasers can also be utilized. The laser medium is disposed between two or more reflective mirrors that define an optical resonator. With each reflection off of the mirrors, the light is further stimulated by the optical pump, leading to its amplification. One of the mirrors is a partial reflector which allows some of the amplified light to exit the cavity as the laser emission, and can also be referred to as an output coupler. The laser output is typically pulsed by such techniques as Q-switching, which can result in substantially higher instantaneous laser power output, and continuous or quasi-continuous operation is also possible.

A laser diode can also be utilized in medical treatment applications. Similar in operation to light emitting diodes, the laser diode is comprised of a p layer and an n layer with an active photon emitting layer in between the p and n layers. Similar to the solid state laser, there are one or more reflectors as well as an output coupler, all of which are incorporated into the semiconductor assembly, with electrical current providing the stimulus to reach the population inversion state.

A conventional laser apparatus suitable for surgical applications is generally comprised of the aforementioned laser energy source and a separate handpiece coupled thereto that can be manually operated by the practitioner. In a basic implementation, the handpiece includes a tip that is in optical communication with the waveguide and the laser energy source. The tip directs the emitted laser onto a target tissue site, and varying shape configurations can yield different output profiles, including simple circular patterns. The laser emission can be directed at any angle that maximizes operator flexibility and comfort in accessing the target tissue site. The optical pathway can be offset from the connecting cable and handpiece axis using different reflector arrangements.

As briefly mentioned above, cutting and ablative efficacy largely depends upon the emitted wavelength and the absorptivity of that particular wavelength by the target tissue. Further, the intensity of the emission, along with the duration of the pulse, must be set to ensure that the tissue does not boil or vaporize, which can lead to greater injury and hemorrhaging. Following irradiation with 4 laser emission, the ablated tissue region is surrounded by a carbonization zone, a zone loosened by vacuoles, a coagulation zone, and a reversibly thermally damaged zone. The formation of the coagulation zone and the resultant hemostasis is advantageous in that tissue can be cut without bleeding.

In order to achieve the best results with the least amount of damage to the surrounding tissue, the laser emission parameters must be optimized for each clinical application. Most laser treatment devices are therefore dedicated to one operation, although supplemental features that do not involve laser emissions are also known. For example, a water supply line and an air supply line can be incorporated into the handpiece to deliver water and air to the target tissue area. This cools the target tissue and helps to remove debris.

To further aid in the removal of debris, vacuum lines can be incorporated. The use of water and air to improve efficacy has not been limited to these objectives, and an alternative cutting mechanism by which laser energy is directed to a distribution of atomized fluid particles located in a volume of space away from the targeted tissue site has been developed and disclosed in, for example, Applicant's U.S. Pat. No. 5,741,247 to Rizoui, the disclosure of which is incorporated herein by reference. The laser energy is understood to interact with the atomized fluid particles causing the same to expand and impart mechanical cutting forces onto the target surface.

To the extent multiple laser emissions can be incorporated into a single laser system, existing laser systems such as those disclosed in U.S. Pat. No. 5,139,494 to Freiberg involve the use of a single laser catheter to the target tissue that is engaged to multiple sources of laser energy, each of which has a different therapeutic effect. The laser sources can be separately activated, and while concurrent operation is indicated, each of the laser energy sources is configured to operate as an independent unit to known effect. Alternatively, some others have contemplated the adjustment of the laser source to enable the selective emission of laser energy at different wavelengths and durations.

Accordingly, there is a need in the art for improved laser treatments utilizing concurrent laser emissions in order to achieve enhanced treatment capabilities that exceed those of such multiple laser emissions operated independently. There is also a need in the art for such laser treatments to achieve improved wound debridement, bacteria reduction and/or inactivation, biostimulation, tissue ablation, coagulation, and biofilm disruption, as well as combinations thereof in a single procedure.

SUMMARY OF THE INVENTION

In accordance with embodiments of the invention, there is provided a treatment device and corresponding treatment method for laser wound healing. The device and method make use of the simultaneous action of multiple laser types and laser wavelengths which are applied to human tissue. The treatment device generally comprises a laser system and a handpiece which is connected to the laser system. The handpiece is designed so that one or multiple laser beams are applied at a relatively small spot and at a relatively high power level, and are surrounded by a relatively large spot of another laser beam with a relatively low power level. In at least one embodiment, the handpiece is adapted to facilitate the emission of a first and a second laser beam together with a third laser beam. The third laser beam is delivered at a different spatial profile in comparison to the first and second laser beams.

In some embodiments, the handpiece can be provided in any one of a multiplicity of different configurations. In one embodiment, the handpiece generally comprises a relatively long central waveguide which is adapted to facilitate the delivery or emission of the first and second laser beams while working in contact with a surface such as subject tissue, or in very close proximity to the surface thereof. In some embodiments, the third laser beam can be delivered to the tissue through a different waveguide, and can effectively surround the application area of the central waveguide. In this regard, in some embodiments, the first and second laser beams can be applied in a smaller central spot, while being surrounded by the third laser beam. By way of example, and not by way of limitation, a handpiece construction which is suitable to facilitate the generation of at least the first and second laser beams along the common central waveguide is described with particularity in Applicant's co-pending U.S. patent application Ser. No. 14/587,955 entitled Dual Wavelength Laser Treatment Device filed Dec. 31, 2013, the disclosure of which is incorporated herein by reference. Other potentially suitable handpiece constructions are found in Applicant's U.S. Pat. No. 7,292,759 to Boutoussov et al; U.S. Pat. No. 7,461,982 to Boutoussov et al; U.S. Pat. No. 7,578,622 to Boutoussov; and U.S. Pat. No. 7,563,226 to Boutoussov, the disclosures of which are also incorporated herein by reference.

In some further embodiments of the invention, the handpiece can comprise various non-contact optical components (e.g., one or more lenses and windows). In some embodiments, the non-contact optical components can collectively function in a manner where the laser beam pattern, after propagation through a free space, forms essentially the same profile on the tissue surface as described above, i.e., the first and second laser beams are applied in smaller central spot, while being surrounded by the third laser beam.

In some embodiments, the first, second and third laser sources can be operated in concert to generate combined laser emissions that synergistically enhance tissue treatment. Furthermore, in some embodiments, the efficacy of treatment with all three laser emissions can potentially be increased with the addition of a water spray that, for ablative forms of treatment, can reduce ablation width, increase ablation depth, and reduce charring that can harm the surrounding tissue. Further, in some embodiments, the use of three laser sources synergistically can provide bactericidal, bio-stimulation or wound healing, and pain reduction benefits. In this regard, although embodiments of the invention described herein can be utilized in relation to wound treatment and healing (e.g., surface debridement, bacteria reduction and bio-stimulation) other clinical applications, like tissue cutting and bacteria reduction can also be effectively implemented. Moreover, in some embodiments, a control system that selectively governs the emissions from the first, second and third laser sources can accomplish the aforementioned functions.

Embodiments of the invention can be best understood by reference to the following detailed description when read in conjunction with the accompanying drawings.

BRIEF DESCRIPTION OF THE DRAWINGS

These, as well as other features of the invention, will become more apparent upon reference to the drawings wherein:

FIG. 4 is a front view showing an emission end of the laser treatment device in accordance with a second embodiment of the invention;

FIG. 5 is a side profile view of the mission end of the laser treatment device shown in FIG. 4, further illustrating an embodiments of a laser emission pattern therefrom; and FIG. 6 depicts another embodiment of a laser emission pattern on a target tissue site as output from the second embodiment of the laser treatment device shown in FIGS. 4 and 5.

Common reference numerals are used throughout the drawings and detailed description to indicate like elements.

DETAILED DESCRIPTION OF THE INVENTION

Figure 1:
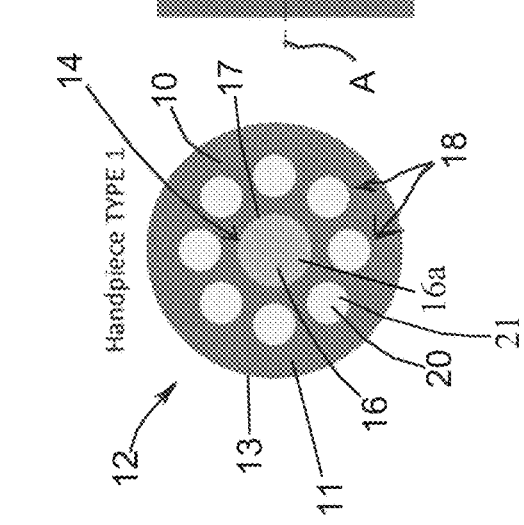
FIG. 1 is a front view showing an emission end of a laser treatment device in accordance with a first embodiment of the invention.

Referring now to the drawings illustrating some embodiments of the invention, and not for purposes of limiting the same, FIG. 1 depicts the emission end 10 of treatment device comprising a handpiece 12 integrated into a multi-wavelength laser treatment device constructed in accordance with a first embodiment of the invention. Though not shown in FIG. 1, in some embodiments, the treatment device will further include a laser beam generating system which is operatively coupled to various laser beam transmission modalities integrated into the handpiece 12, as will be described in more detail below.

As shown in FIG. 1, in some embodiments, the handpiece 12 can comprise a main body 11 where a portion of the handpiece 12 defining the emission end 10 can comprise a generally cylindrical configuration defining an axis A. Therefore, in some embodiments, the emission end 10 can comprise a generally circular profile. However, those of ordinary skill in the art will recognize that this particular shape only illustrates some embodiments, and the shapes can be modified in the treatment device of the first embodiment without departing from the spirit and scope of the invention.

Figure 2:
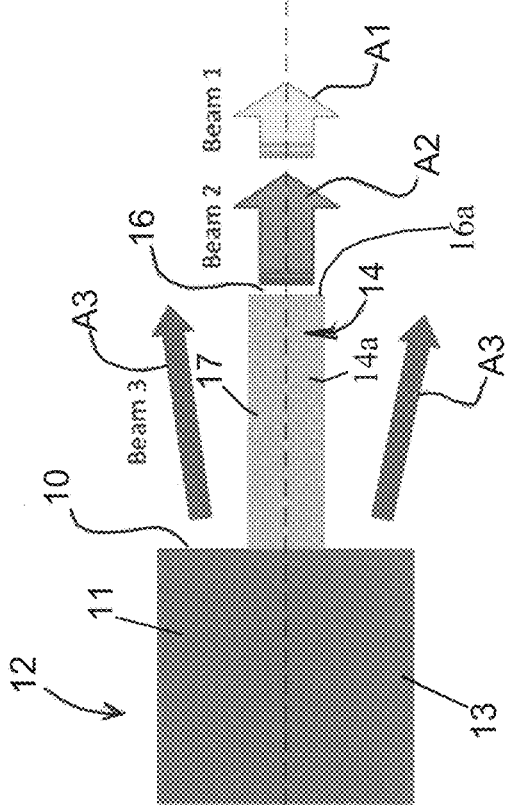
FIG. 2 is a side profile view of the emission end of the laser treatment device shown in FIG. 1, further illustrating an embodiment of a laser emission pattern therefrom.

Referring to FIG. 2, in some embodiments, protruding from the approximate center of the emission end 10 of the handpiece 12 and extending along the axis A is the distal end portion 14*a* of an elongate, central waveguide 14 of the treatment device (comprising handpiece 12), at least a portion of which is integrated into the handpiece 12. In some embodiments, the central waveguide 14 has a generally circular cross-sectional configuration, and defines a distal emission or output end 16. Thus, in some embodiments, at least that portion of the axis of the central waveguide 14 defined by the distal end portion 14*a* thereof protruding from the emission end 10 is coincident with the axis A. Though not shown, in some embodiments, in accordance with a variant of the treatment device of the first embodiment, the output end 16 of the central waveguide 14 can be substantially flush or substantially continuous with the emission end 10, rather than protruding therefrom. Further, in some other embodiments, the central waveguide 14 can comprise a diameter that is larger or smaller than illustrated. Thus, the output end 16 of the central waveguide 14 can also comprise an area that is relatively larger or smaller than illustrated in some embodiments.

In some embodiments of the invention, the treatment device of the first embodiment comprising the handpiece 12 can comprise a central waveguide 14 that can be adapted to facilitate the delivery or emission of at least one laser beam. For example, in some embodiments of the invention, the treatment device of the first embodiment comprising the handpiece 12 can comprise a central waveguide 14 that can be adapted to facilitate the delivery of two laser beams from an output emission surface 16*a* of the output end 16. For example, in FIG. 2, the first laser beam as emitted from an output emission surface 16*a* of the output end 16 of the central waveguide 14 is identified by the arrow labeled A1, with the second laser beam as emitted from the output emission surface 16*a* of the output end 16 of the central waveguide 14 is identified by the arrow labeled A2. In some embodiments, the first laser beam A1 and the second laser beam 42 can be substantially coincident and coaxial. In some other embodiments, the first laser beam A1 and the second laser beam A2 can be at least partially coincident and coaxial. In some other embodiments, the first laser beam A1 and the second laser beam A2 can be substantially parallel. In some other embodiments, the first laser beam A1 and the second laser beam A2 can be divergent.

In some embodiments of the invention, the treatment device can comprise a handpiece 12 that can further comprise a plurality of peripheral light pipes or waveguides. For example, in some embodiments of the invention, a plurality of peripheral light pipes or waveguides 18 can be at least partially integrated into the handpiece 12. Referring to FIG. 1, in some embodiments, the handpiece 12 can comprise eight peripheral waveguides 18 positioned within the main body 11. Those of ordinary skill in the art will recognize that this number can be increased or decreased without departing from the spirit and scope of the invention, and other embodiments can include more or fewer peripheral waveguides 18 than shown. In some embodiments, one or more peripheral waveguides 18 can be positioned in the main body 11 between the outer edge 17 of the central waveguide and the outer surface 13 of the main body 11. In some embodiments, the peripheral waveguides 18 can be positioned to at least partially encircle the central waveguide 14 (i.e., the central waveguide 14 is concentrically positioned with the peripheral waveguides 18). In some embodiments, the peripheral waveguides 18 are substantially equally spaced (as depicted in FIG. 1). In other embodiments, at least some peripheral waveguides 18 are unequally spaced.

In some embodiments of the invention, at least one of the peripheral waveguides 18 can comprise a generally circular cross-sectional configuration. Further, in some embodiments, at least one of the peripheral waveguides 18 can comprise a generally circular cross-sectional configuration that defines a distal emission or output end 20. For example, as illustrated in FIG. 1, in some embodiments, the handpiece 12 can comprise a main body 11 including eight peripheral waveguides 18 that can comprise a generally circular cross-sectional configuration defining a distal emission or output end 20. Moreover, in some embodiments, at least one of the peripheral waveguides 18 can be positioned in the main body 11 to be substantially flush or substantially continuous with the emission end 10 rather than protruding therefrom.

In some embodiments of the invention, the treatment device of the first embodiment comprising the handpiece 12 includes peripheral waveguides 18 that are adapted to emit a third laser beam from an output emission surface 21 of output ends 20 thereof. For example, referring to FIG. 2, some embodiments include a third laser beam (identified by the arrows labeled A3) that is emitted from the output ends 20 of the peripheral waveguides 18 through at least one output emission surface 21. The depiction represents the example embodiment of the collective emission from the plurality of peripheral waveguides 18 (i.e., the total emission of the third laser beam A3 is derived from output from the eight peripheral waveguides 18). In some other embodiments, the third laser beam A3 can comprise emission of laser radiation from less than the eight peripheral waveguides 18 depicted in FIG. 1. For example in some embodiments, the third laser beam A3 can comprise laser radiation from between one and seven peripheral waveguides 18. Moreover, in some other embodiments, additional peripheral waveguides 18 can be included to emit laser radiation that can fin m part of the third laser beam A3.

Though not shown, in some embodiments, the laser beam generating system included in the treatment device of the first embodiment can include at least three separate, conventional laser sources. In some embodiments, the first and second laser sources can be operatively coupled to an input end of the central waveguide 14, with the third laser source being operatively coupled to input ends of the peripheral waveguides 18. In some embodiments of the invention, the first laser source can comprise a diode laser. Further, in some embodiments, the operational parameters of the first laser source can comprise a wavelength of about 940 nm in a continuous wave (CW) mode and at an average output power in a range of from about 1 W to about 10 W. In some further embodiments, the second laser source can be a solid state Er, Cr:YSGG laser, where the operational parameters can be at a wavelength of about 2.78 µm in a short pulse mode (H mode) in a range of from about 5 Hz to about 20 Hz, and at an average output power in a range of from about 2 W to about 10 W. In some further embodiments, the third laser source can be a diode laser or LED, where the operational parameters can be a wavelength of about 630 nm, or about 810 nm, or about 940 nm in a continuous wave (CW) mode, and at an average output power in a range of from about 50 mW to about 1000 mW.

Figure 3:
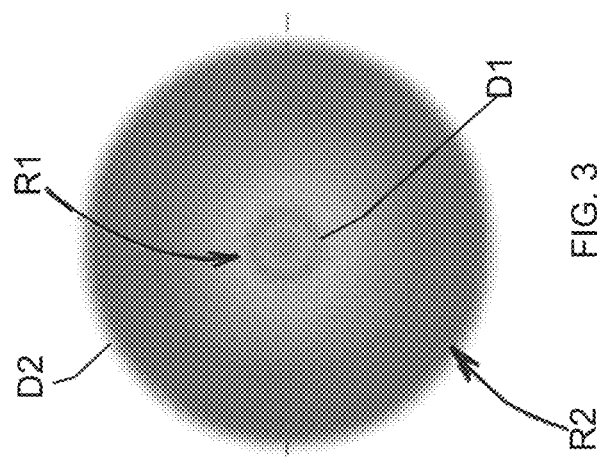
FIG. 3 depicts an example laser emission pattern on a target tissue site as output from the first embodiment of the laser treatment device shown in FIGS. 1 and 2.

Referring now to FIG. 3, in some embodiments, with at least partial integration of the central and peripheral waveguides 14, 18 therein, the handpiece 12 of the treatment device of the first embodiment can be configured so that the first and second laser beams A1, A2 can be applied as a spot or emission pattern comprising a first diameter D1 comprising a first power level, and surrounded by the third laser beam A3 spot or emission pattern comprising a second diameter D2 comprising a second power level. In some embodiments, the handpiece 12 can be adapted to facilitate the emission of the first and second laser beams together, with the third laser beam being delivered at a different spatial profile in comparison to the first and second laser beams. As depicted in FIG. 3, in some embodiments, the central area or region of the emission pattern labeled as R1 can be created by the combined emissions of the first and second laser beams (A1, A2) from the central waveguide 14. In some embodiments, this central region R1 can be at least partially encircled by a peripheral area or region of the emission pattern labeled as R2 which is created by the emission of the third laser beam from the peripheral waveguides 18.

In some embodiments, due to the protrusion of the central waveguide 14 from the emission end 10 of the handpiece 12, during operation, the output end 16 of the central waveguide 14 can be configured to be in contact with the tissue to be treated or disposed in very close proximity thereto. Thus, in some embodiments, there is a limited measure, if any, of propagation of the combined first and second laser beams A1, A2 emitted from the output end 16 of the central waveguide 14 through free space prior to the same defining the central region R1 of the emission pattern on the tissue. In contrast, in some embodiments, in view of the output ends 20 of the peripheral waveguides 18 each being substantially flush with the emission end 10 of the handpiece 12, a greater measure of propagation of the third laser beam A3 collectively emitted from the output ends 20 of the peripheral waveguides 18 through free space can occur prior to the third laser beam A3 defining the peripheral region R2 of the emission pattern on the tissue.

Some embodiments of the invention include a treatment device of the first embodiment where the first laser beam A1 having a first beam characteristic can be emitted as a result of the activation of the first laser source. Similarly, in some embodiments, the second laser beam A2 can be emitted as a result of the activation of the second laser source that can have a second beam characteristic, with the third laser beam emitted as a result of the activation of the third laser source having a third beam characteristic. As utilized herein, the term "beam characteristic" refers to any one or combination of emission and operational parameters, including wavelength, divergence, beam diameter, output power, pulse duration (whether periodic or continuous) and duty cycle, pulse frequency, and any other parameters that can be adjusted to achieve different therapeutic effects. In this regard, in some embodiments, the beam characteristics of the laser beams generated by the first, second and third laser sources within the treatment device can differ from each other, meaning that a least one of the emission and operational parameters specified above can vary within such laser beams.

Some embodiments of the invention include a configuration of the treatment device of the first embodiment, including but not limited to the handpiece 12 thereof, that can enable a combination of the two separate emissions of the first laser source and the second laser source for output from the common central waveguide 14. It will be recognized by those having ordinary skill in the art that beam divergence is generally the inverse of the wavelength. As indicated above, the first laser source and the second laser source will typically not be operated at exactly the same wavelength. Accordingly, based on the differing output wavelengths alone, beam divergence is likewise understood to differ between the first laser source and the second laser source. In some embodiments, beam divergence can also depend on the particulars of the laser energy source, and further variability can be introduced because of the differing laser types (e.g., the first laser source A1 can comprise a diode configuration, while the second laser source can comprise a solid state configuration). As indicated above, in some embodiments, the handpiece 12 can be configured to emit the first and second laser beams A1, A2 with dissimilar beam characteristics characterized by different wavelengths and divergences that can be combined into the final transmission path defined by the central waveguide 14.

In some further embodiments (not shown), the handpiece 12 of the treatment device of the first embodiment can further be optionally outfitted with a delivery system (e.g., a water supply line and/or an air supply line) to facilitate the delivery of water and air to a target tissue area concurrently with the delivery of laser energy. A more comprehensive treatment of applicant's existing technology describing the structural and functional features of such delivery systems in the context of laser hand-pieces can be found in U.S. Pat. No. 5,741,247 to Rizoiu et al., U.S. Pat. No. 7,702,196 to Boutoussov, et al., and U.S. Pat. No. 8,485,818 to Boutoussov, et al., the disclosures of which are incorporated herein by reference.

Some embodiments of the invention include a treatment device that can comprise a handpiece 112 configured to emit at least one laser beam. For example, referring to FIG. 4, some embodiments of the invention include a handpiece 112 comprising an emission end 110 of the second embodiment of a multi-wavelength laser treatment device. Though not shown in FIG. 4, as in the laser treatment device of the first embodiment comprising the handpiece 12, the second embodiment of the treatment device including the handpiece 112 can include a laser beam generating system which is operatively coupled to the handpiece 112 portion of the treatment device. In some embodiments, a portion of the handpiece 112 defining the emission end 110 can include a generally cylindrical configuration defining an axis A', the emission end 110 thus having a generally circular profile. However, those of ordinary skill in the art will recognize that this particular shape illustrates some illustrative embodiments and can be modified without departing from the spirit and scope of the invention.

Referring to FIGS. 4 and 5, in the treatment device of the second embodiment, the handpiece 112 can comprise various non-contact optical components (e.g., one or more lenses and windows) which can function in a manner so that after propagation through free space, the laser beam pattern emitted from the handpiece 112 can form essentially the same profile on the tissue surface as described above and shown in FIG. 3 (i.e., where the first and second laser beams A1, A2 can be applied at to a spot or emission pattern comprising a first diameter D1 comprising a first power level, and surrounded by the third laser beam A3 spot or emission pattern comprising a second diameter D2 comprising a second power level). More particularly, FIGS. 4 and 5 each depict an optical window 122 that can be integrated into the main body 111 of the handpiece 112 so as to define at least a portion of the emission end 110 thereof. In this regard, in some embodiments, the optical window 122 can comprise an outer surface 127 and a generally circular configuration forming a distal emission or output end 126, and can define an axis which is coincident with the axis A'.

Further, in some embodiments, the outer diameter of the optical window 122 can be smaller than the outer diameter of the main body 111 of the handpiece 112 defining the emission end 110. Moreover, in some embodiments, the optical window 122 can be positioned recessed into the main body 111. For example, in some embodiments, the main body 111 can comprise a recess 111a into which the optical window 122 can be positioned. In some embodiments of the invention, the emission end 110 can include the output end 126 of the optical window 122 that defines the outer emission surface 124. Further, in some embodiments, the optical window 122 can be positioned in the main body 111 (within the recess 111a) so that the outer emission surface 124 can be substantially flush or substantially continuous with an outer surface 110a portion of the emission end 110 defined by the remainder of the handpiece 112.

In some embodiments of the invention, the optical window 122 can be adapted to facilitate the delivery or emission of at least one laser beam. For example, in some embodiments, the optical window 122 can be adapted to facilitate the delivery or emission of at least a first, second and third laser beams from the outer emission surface 124 thereof. Referring to FIG. 5, the first laser beam can be emitted from the outer emission surface 124 of the optical window 122 and is identified by the arrow labeled A1'. Further, the second laser beam can be emitted from the outer emission surface 124 of the optical window 122 identified by the arrow labeled A2'. Further, the third laser beam emitted from the outer emission surface 124 of the optical window 122 is identified by the arrows labeled A3'.

In some embodiments, the treatment device of the second embodiment (comprising handpiece 112) can comprise can include three laser sources. In some embodiments, the functional attributes of these first, second and third laser sources can be substantially the same as those described above in relation to the first, second and third laser sources, respectively, of treatment device constructed in accordance with the first embodiment of the invention (comprising handpiece 12). In some embodiments, the treatment device of the second embodiment, and in particular the handpiece 112 thereof, can be configured to facilitate the operative coupling of the first, second and third laser sources to the optical window 122.

Referring now to FIG. 6, some embodiments of the treatment device of the second embodiment, including the handpiece 112 thereof, can be configured so that the first and second laser beams can be applied at a first spot and at a specific first power level, and are surrounded by a second spot of the third laser beam with a second power level. In some embodiments, the handpiece 112 can be adapted to facilitate the emission of the first and second laser beams together (forming the first spot), with the third laser beam being delivered at a different spatial profile in comparison to the first and second laser beams. In FIG. 6, the central area or region of the emission pattern labeled as R1' can be created by the combined emissions of the first and second laser beams from the optical window 122 (i.e. forming the first spot). This central region R1 is circumvented by a peripheral area or region of the emission pattern labeled as R2 which is created by the emission of the third laser beam from the optical window 122 (i.e., the second spot).

In some embodiments, due to the outer emission surface 124 of the optical window 122 being flush with the remainder of the emission end 110 in the treatment device of the second embodiment, in normal device operation, there can be a prescribed measure of propagation of the combined first and second laser beams and the third laser beam emitted from the outer emission surface 124 of the optical window 122 through free space prior to the same defining the central and peripheral regions region R1' and R2', respectively, of the laser emission pattern on the tissue.

In some embodiments, in the treatment device of the second embodiment (comprising handpiece 112), the first, second and third laser beams emitted as a result of the activation of respective first, second and third laser sources can have dissimilar beam characteristics as discussed above in relation the treatment device of the first embodiment (comprising handpiece 12). Further, in some embodiments, the configuration of the treatment device of the second embodiment, including but not limited to the handpiece 112 thereof, will allow for the efficient and effective combination of the two separate emissions of the first laser source and the second laser source for output from the optical window 122.

Moreover, as in the treatment device of the first embodiment, though not shown in the FIGS. 4-6, the handpiece 112 of the treatment device of the second embodiment can further be optionally outfitted with a delivery system (e.g., a water supply line and an air supply line) as allows it to facilitate the delivery of water and air to the target tissue area concurrently with the delivery of laser energy thereto.

In some embodiments of the invention, the combined emissions from the three laser sources are understood to have a synergistic effect beyond that which is understood to be possible from applying just one laser source. As indicated above, in some embodiments, the first laser source can be a diode laser having a wavelength of about 940 nm, while the second laser source can be a solid state Er, Cr:YSGG laser having a wavelength of about 2.78 μM. Furthermore, in some embodiments, the third laser source can be a diode laser or LED having a wavelength of about 630 nm, about 810 nm, or about 940 nm. Notwithstanding these specific configuration values, it will be appreciated by those having ordinary skill in the art that such particulars can be modified to suit the desired application. As such, these configuration values are presented by way of example only and not of limitation.

In some embodiments of the invention, the treatment device can be designed and used for wound treatment and healing, in particular, surface debridement, bacteria reduction, and bio-stimulation. In some embodiments, the laser energy emitted from the emission end 10, 110, which is understood to have wavelength, pulse duration, and power level parameters as described above in relation to the handpieces 12, 112, can be directed to a target site by the practitioner. In accordance with the invention, the particular application of the first and second laser beams applied at a relatively small spot and at a relatively high power level, together with the surrounding relatively large spot of the third laser beam operated at a relatively low power level is understood to suitable for achieving these objectives. However, other applicable clinical applications include tissue cutting (and related bacteria reduction).

In applicant's co-pending U.S. patent application Ser. No. 14/587,955 entitled Dual Wavelength Laser Treatment Device filed Dec. 31, 2013 noted above, various synergistic effects of applying multiple laser sources to a target tissue site are described. For example, tissue ablation can be enhanced, particularly with respect to ablation rate, precision, and control, with the application of a first laser emission and a second laser emission. Further, the efficacy of the laser treatment can be further improved with the inclusion of positive airflow and water spray. Furthermore, synergistic bactericidal effects were also disclosed, with the application of the first laser emission substantially weakening certain bacteria and the application of the second laser emission killing the weakened bacteria, whereas the separate application of either laser emission being less effective.

In some embodiments of the invention, other synergistic effects of utilizing multiple laser energy sources pertaining to bio-stimulation and wound healing can be facilitated by the handpieces 12, 112 described herein. For example, in some embodiments, the application of higher power, penetrating laser radiation utilizing diode laser modalities at ablative or non-ablative levels can result in the application of lower level laser radiation to surrounding tissue three-dimensionally as a consequence of the absorption and scattering effects therein. In some embodiments, the concurrent application of YSGG laser pulses also at ablative or sub-ablative power levels is understood to generate pressure waves within the water-rich tissue, and increase the effect of the aforementioned laser light therapy because of the mechanical stimulation of the tissue cells.

In accordance with various embodiments of the invention, the treatment devices can include operational parameters for achieving the aforementioned clinical objectives. In particular, for applications involving a combination of wound debridement, bacteria reduction, and bio-stimulation, the first laser emission can include an output power of about 9 W in a continuous (CW) mode. Further; in some embodiments, the second laser emission can include an output power of about 10 W that is pulsed at about 15 Hz. In some embodiments, the third laser emission can have an output power of about 50 to about 1000 mW. In this configuration, airflow and water flow can be used as desired.

In some embodiments, for applications involving a combination of improved tissue ablation, coagulation, and bio-stimulation, other operational parameters can be used. For example, in some embodiments, the first laser emission can include an output power of about 10 W and can be operated in a continuous mode. In some embodiments, the second laser emission can include an output power of about 10 W, and can be pulsed at about 20 Hz. Airflow and water flow can be used for this treatment modality. Further, in some embodiments, the third laser emission, like the preceding application requiring a combination of wound debridement, bacteria reduction, and bio-simulation, can be operated between about 50 to about 1000 mW in a continuous mode.

In some embodiments, the air flow can be between 0.1 to 5 liters/minute, and the water flow can be between 0.1 to 5 milliliters/minute. In other embodiments, the water flow and/or the airflow can be outside of these ranges. For example, in some embodiments, the air flow can be less than 0.1 liters/minute or greater than 5 liters/minute, and the water flow can be less than 0.1 milliliters/minute or greater than 5 milliliters/minute.

In some embodiments, applications relating to the aforementioned biofilm disruption and bacterial inactivation can include other operational parameters. In particular, in some embodiments, the first laser emission has an output power of about 1 W, and can be operated in a continuous mode. Further, in some embodiments, the second laser emission can include an output power of about 2 W, and can be operated in a pulsed mode. In some embodiments, the pulse frequency of the second laser emission can be about 5 Hz. In some embodiments, the third laser emission likewise can include an output power of between about 50 to about 1000 mW operated in a continuous mode. In this variation, no airflow and no water flow is required, and may not be used.

In some embodiments of the invention, the aforementioned sequencing of driving the multiple laser energy sources can be variously implemented via signals from a control unit (not shown). The control unit may include a general purpose data processor that executes pre-programmed instructions stored on an associated memory device that implement such control methods. Further, in addition to the instructions for driving the laser energy sources, the control unit/data processor can further include instructions for user interface modules that can receive configuration and operating inputs from the practitioner. Only one driving sequence has been illustrated, but due to the flexibility afforded in a software-based control system, any suitable Laser energy delivery sequence can be substituted, Other types of sequencing can be used for different therapeutic advantages that can specific for particular surgical operations. The control unit is understood to measure readings from various sensors that trigger appropriate responses (up to and including terminating the laser emissions) upon detecting hazardous operating conditions.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

What is claimed is:
1. A method for laser treatment of a target tissue site, the method comprising:
applying a first laser emission to the target tissue site, the first laser emission alone having a first treatment effect on the target tissue site;

applying a second laser emission to the target tissue site, the second laser emission being applied within a predetermined time period of applying the first laser emission during which the target tissue site is subject to the first treatment effect from the first laser emission; and applying a third laser emission to the target tissue site concurrently with the first laser emission, the third laser emission alone having a third treatment effect on the target tissue site; and wherein each of the first laser emission, the second laser emission, and the third laser emission is defined by a respective set of beam characteristics, one of the beam characteristics being a spatial profile, a first spatial profile of the first laser emission being substantially the same as a second spatial profile of the second laser emission, and a third spatial profile of the third laser emission being larger than the first spatial profile of the first laser emission and the second spatial profile of the second laser emission.

2. The method of claim 1, wherein:

at least another one of the beam characteristics of each of the first laser emission, the second laser emission, and the third laser emission are different; and the first laser emission, the second laser emission, and the third laser emission have a synergistic treatment effect different from first treatment effect, the second treatment effect, and the third treatment effect, with the first treatment effect, the second treatment effect, and the third treatment effect being non-linearly enhanced by each other.

3. The method of claim 1, wherein the first laser emission, the second laser emission, and the third laser emission are combined and emitted from a single output of a treatment device.

4. The method of claim 1, wherein one of the beam characteristics is beam wavelength, a first beam wavelength of the first laser emission is 940 nm, a second beam wavelength of the second laser emission is 2.78 µm, and a third beam wavelength of the third laser emission is selected from a group consisting of 630 nm, 810 nm, and 940 nm.

5. The method of claim 4, wherein:

the first laser emission is generated from a diode laser source; and the second laser emission is generated from a solid state laser source.

6. The method of claim 5, wherein the third laser emission is generated from a diode laser source.

7. The method of claim 5, wherein the third laser emission is generated from a light emitting diode (LED) laser source.

8. The method of claim 4, wherein a combination of the first treatment effect, the second treatment effect, and the third treatment effect includes a combination of wound debridement, bacteria reduction, and bio-stimulation.

9. The method of claim 8, wherein:

the first laser emission has an output power of approximately 9 W;

the second laser emission has an output power of approximately 10 W;

the third laser emission has an output power between 50 mW to 1000 mW.

10. The method of claim 9, wherein the second laser emission is pulsed at approximately 15 Hz.

11. The method of claim 8, further comprising:

applying an air flow and a water flow to the tissue site.

12. The method of claim 11, wherein:

the air flow is between 0.1 to 5 liters/minute; and the water flow is between 0.1 to 5.0 milliliters/minute.

13. The method of claim 4, wherein a combination of the first treatment effect, the second treatment effect, and the third treatment effect includes a combination of tissue ablation, coagulation, and bio-stimulation.

14. The method of claim 13, wherein:

the first laser emission has an output power of approximately 10 W;

the second laser emission has an output power of approximately 10 W; and the third laser emission has an output power between 50 mW to 1000 mW.

15. The method of claim 14, wherein the second laser emission is pulsed at approximately 20 Hz.

16. The method of claim 14, wherein the second laser emission is pulsed at approximately 5 Hz.

17. The method of claim 13, further comprising:

applying an air flow and a water flow to the tissue site.

18. The method of claim 17, wherein:

the air flow is between 0.1 to 5 liters/minute; and the water flow is between 0.1 to 5.0 milliliters/minute.

19. The method of claim 4, wherein a combination of the first treatment effect, the second treatment effect, and the third treatment effect includes a combination of biofilm disruption and bacterial inactivation.

20. The method of claim 19, wherein:

the first laser emission has an output power of approximately 1 W;

the second laser emission has an output power of approximately 2 W; and the third laser emission has an output power between 50 mW to 1000 mW.

* * * * *